United States Patent
Hatchett et al.

(10) Patent No.: US 10,537,462 B1
(45) Date of Patent: Jan. 21, 2020

(54) COLOSTOMY APPLIANCE WITH FLUSHABLE INSERT

(71) Applicant: Wildhatch, LLC, Tulsa, OK (US)

(72) Inventors: John D. Hatchett, Hominy, OK (US); Scott A. Fengler, Tulsa, OK (US)

(73) Assignee: Wildhatch, LLC, Tulsa, OK (US)

( * ) Notice: Subject to any disclaimer, the term of this patent is extended or adjusted under 35 U.S.C. 154(b) by 1050 days.

(21) Appl. No.: 14/934,883

(22) Filed: Nov. 6, 2015

(51) Int. Cl.
*A61F 5/448* (2006.01)

(52) U.S. Cl.
CPC .................. *A61F 5/448* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,078,180 A * | 4/1937 | Kronenberg | ........... | A61H 35/04 604/28 |
| 2,485,184 A * | 10/1949 | Blackman | ........... | A61M 1/0062 128/200.22 |
| 2,503,056 A | 4/1950 | Lay | | |
| 3,089,493 A | 5/1963 | Galindo | | |
| 3,100,488 A | 8/1963 | Orowan | | |
| 3,690,320 A * | 9/1972 | Riely | ........... | A61F 5/4407 604/333 |
| 4,816,027 A * | 3/1989 | Gilchrist | ........... | A61F 5/445 604/332 |
| 4,826,495 A * | 5/1989 | Petersen | ........... | A61F 5/441 604/333 |
| 5,423,782 A | 6/1995 | Wolrich | | |
| 5,591,144 A * | 1/1997 | Smith | ........... | A61F 5/445 604/327 |
| 5,690,622 A * | 11/1997 | Smith | ........... | A61F 5/441 128/DIG. 24 |
| 5,785,695 A * | 7/1998 | Sato | ........... | A61F 5/448 604/338 |
| 5,865,819 A * | 2/1999 | Cisko, Jr. | ........... | A61F 5/445 604/327 |
| 5,938,647 A * | 8/1999 | Smith | ........... | A61F 5/445 128/DIG. 24 |
| 5,964,223 A * | 10/1999 | Baran | ........... | A61M 16/0463 128/200.14 |
| 6,902,551 B2 | 6/2005 | Hansen et al. | | |
| 7,214,217 B2 | 5/2007 | Pedersen et al. | | |
| 7,416,543 B2 * | 8/2008 | Brown | ........... | A61L 28/0034 604/332 |
| 7,422,578 B2 * | 9/2008 | Shan | ........... | A61F 5/448 604/332 |

(Continued)

*Primary Examiner* — Tatyana Zalukaeva
*Assistant Examiner* — Guy K Townsend
(74) *Attorney, Agent, or Firm* — Gable Gotwals

(57) ABSTRACT

The present invention relates to a colostomy appliance with a flushable insert that can be removed and replaced without removing the outer bag, allowing for quicker, easier, and more sanitary disposal of fecal waste. The appliance is comprised of a faceplate with an attachment ring that has a lip and a catch, an outer colostomy bag with top and bottom openings that can be temporarily closed, and an insert made of a flushable material. The insert has an opening that fits over the attachment ring and is aligned and secured in its proper position inside the bag by the lip and the catch of the attachment ring. The present invention also provides a method for using the flushable insert with a colostomy appliance.

6 Claims, 5 Drawing Sheets

(56) References Cited

U.S. PATENT DOCUMENTS

| | | | |
|---|---|---|---|
| 7,517,339 B2 | 4/2009 | Pedersen et al. | |
| 7,604,622 B2 | 10/2009 | Pedersen et al. | |
| 7,722,586 B2 | 5/2010 | Mullejans et al. | |
| 7,819,850 B2 | 10/2010 | Mullejans et al. | |
| 7,931,631 B2 | 4/2011 | Pedersen et al. | |
| 8,105,298 B2 | 1/2012 | Mullejans et al. | |
| 8,118,797 B2 | 2/2012 | Giori et al. | |
| 8,343,120 B2* | 1/2013 | Smith | A61F 5/448 156/254 |
| 8,914,912 B2* | 12/2014 | Stevenson | A41D 13/012 2/82 |
| 9,539,137 B2* | 1/2017 | Smith | A61F 5/441 |
| 2003/0023210 A1 | 1/2003 | Bedard et al. | |
| 2003/0153883 A1* | 8/2003 | Hansen | A61F 5/445 604/337 |
| 2004/0059306 A1* | 3/2004 | Tsai | A61F 5/4404 604/332 |
| 2004/0193122 A1* | 9/2004 | Cline | A61F 5/445 604/332 |
| 2005/0004539 A1* | 1/2005 | Brown | A61L 28/0034 604/327 |
| 2005/0113770 A1* | 5/2005 | Pedersen | A61F 5/448 604/332 |
| 2005/0177119 A1* | 8/2005 | Tsai | A61F 5/445 604/332 |
| 2007/0005032 A1* | 1/2007 | Shan | A61F 5/448 604/342 |
| 2008/0154183 A1* | 6/2008 | Baker | A61M 1/0058 604/28 |
| 2008/0221507 A1* | 9/2008 | Hoke | A61H 35/04 604/28 |
| 2008/0294129 A1* | 11/2008 | Giori | A61F 5/445 604/332 |
| 2009/0163885 A1* | 6/2009 | Pedersen | A61F 5/448 604/333 |
| 2009/0163886 A1* | 6/2009 | Therkelsen | A61F 5/448 604/342 |
| 2009/0281483 A1* | 11/2009 | Baker | A61M 1/0058 604/28 |
| 2009/0281485 A1* | 11/2009 | Baker | A61M 1/0058 604/35 |
| 2010/0152653 A1* | 6/2010 | Hoke | A61M 1/0058 604/94.01 |
| 2011/0054425 A1* | 3/2011 | Smith | A61F 5/448 604/342 |
| 2011/0238024 A1* | 9/2011 | Smith | A61F 5/445 604/336 |
| 2012/0172823 A1* | 7/2012 | Smith | A61F 5/441 604/333 |
| 2012/0234485 A1* | 9/2012 | Smith | A61F 5/448 156/252 |
| 2012/0330239 A1* | 12/2012 | Hoke | A61H 35/04 604/151 |
| 2013/0053803 A1* | 2/2013 | Willoughby | A61F 5/445 604/337 |
| 2014/0230125 A1* | 8/2014 | Stevenson | A41D 13/012 2/82 |
| 2015/0224246 A1* | 8/2015 | Layer | A61M 3/0283 604/30 |
| 2016/0129205 A1* | 5/2016 | Shahaf | A61M 11/02 128/200.23 |
| 2016/0278969 A1* | 9/2016 | De Weert | A61F 5/441 |
| 2016/0303308 A1* | 10/2016 | Layer | A61M 3/0258 |
| 2017/0028144 A1* | 2/2017 | Flickinger | A61M 3/0279 |
| 2017/0112658 A1* | 4/2017 | Hosono | A61F 5/448 |
| 2018/0093034 A1* | 4/2018 | Tsang | A61M 3/0262 |

\* cited by examiner

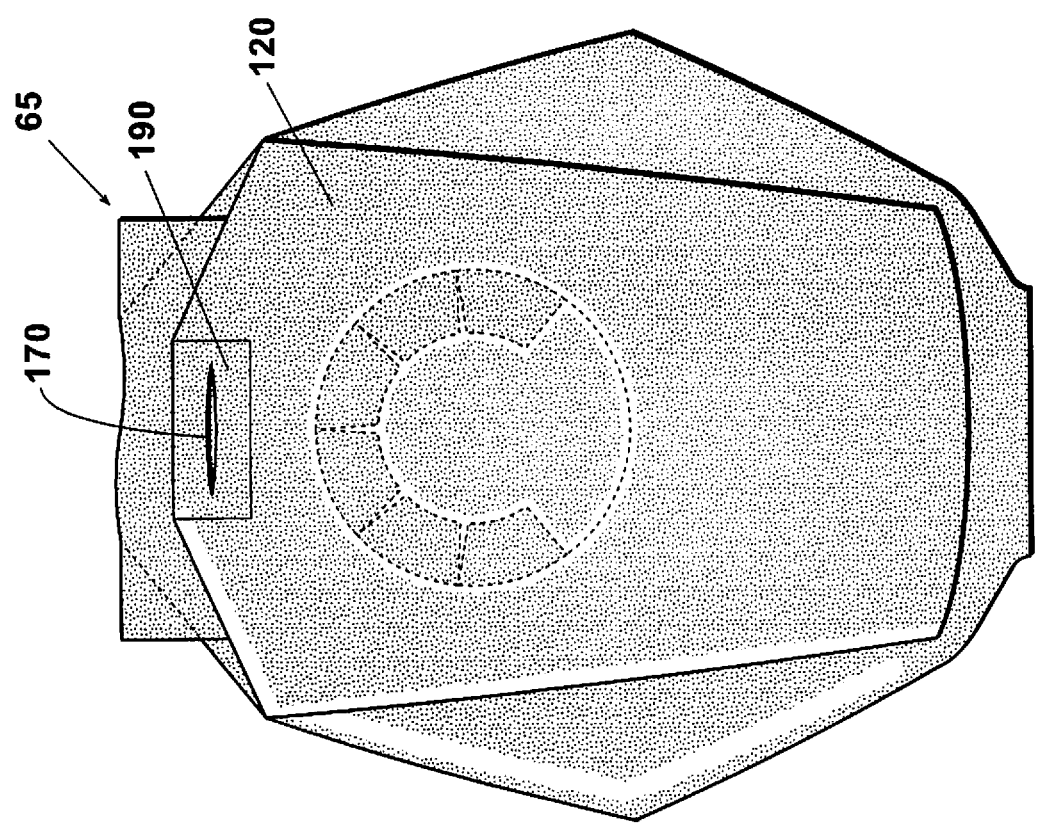
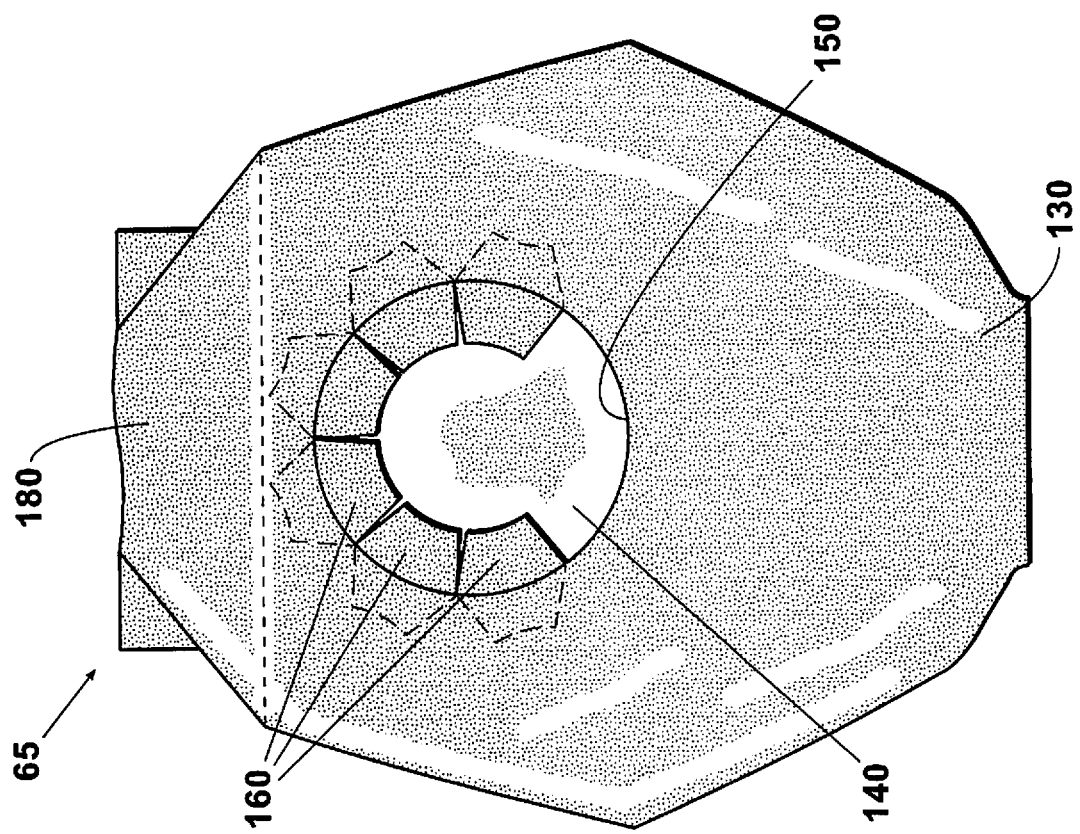

COLOSTOMY APPLIANCE WITH FLUSHABLE INSERT

FIELD OF THE INVENTION

The present invention generally relates to devices, systems, and methods for using a colostomy appliance. In particular, the present invention relates to a colostomy appliance with a flushable insert that can be removed and replaced without removing the outer bag, allowing for quicker, easier, and more sanitary disposal of fecal waste.

BACKGROUND OF THE INVENTION

A colostomy is a surgical procedure in which a stoma is formed by drawing the healthy end of the large intestine or colon through an incision in the abdominal wall and suturing it into place. The stoma, in conjunction with an attached colostomy appliance, provides an alternate channel for fecal waste to leave the body.

Colostomy appliances generally include a faceplate and a colostomy bag. The faceplate is attached to the patient and connected to a waterproof colostomy bag that receives the fecal waste. In a one-piece system, the faceplate and the bag are joined together as a single unit. As a result, both the faceplate and the bag must be removed whenever it is necessary to change the bag. In a two-piece system, the faceplate is removably connected to the bag such that the bag can be emptied or changed without removing the faceplate from the patient.

There are multiple difficulties associated with emptying or changing the bag of a traditional colostomy appliance. The process can be unsanitary and time-consuming, particularly for patients who lack dexterity. In addition, the patient may need access to additional materials and supplies, such as water and squirt bottles, in order to thoroughly clean the bag. These difficulties may be compounded when the patient is using a public restroom or a restroom away from his or her home. Finally, disposing of fecal waste and used bags in the garbage may also be unsanitary and embarrassing to the patient.

Thus, there is a need for a modified colostomy appliance that can be changed quickly, easily, and cleanly without the need for additional materials or supplies. In addition, there is a need for an appliance that provides for the disposal of fecal waste by flushing it down the toilet.

SUMMARY OF THE INVENTION

The present invention provides a colostomy appliance that has been modified to incorporate a flushable insert that can be removed and replaced without removing the outer colostomy bag. The appliance is comprised of a faceplate with an attachment ring that has a lip and a catch for aligning and securing the insert in the proper position within the bag. The appliance is further comprised of an outer colostomy bag with top and bottom openings that can be temporarily closed and a flushable insert with an opening that fits over the attachment ring.

The present invention also provides a flushable insert for a colostomy appliance. The insert has front and back panels, each comprised of a flushable material, that are joined together to form a pouch that fits inside the outer colostomy bag. The back panel has an opening that receives the attachment ring of the faceplate, while the front panel has a slot that fits over the catch on the attachment ring.

The present invention also provides a method for using the flushable insert with a colostomy appliance. The steps of the method include, but are not limited to, attaching the faceplate with the attachment ring to a patient's body, opening the outer colostomy bag that is attached to the faceplate, placing the flushable insert inside the bag, using the catch and lip of the attachment ring to properly align and secure the insert, and closing the bag until the insert is ready for removal. The steps associated with removing and replacing the insert include opening the outer colostomy bag, disconnecting the insert from the catch on the attachment ring, folding the upper portion of the insert's back panel over the insert's front panel, removing the insert from the bag, flushing the insert down the toilet, and placing and aligning a new insert in the bag.

These and other features, aspects, and advantages of the present invention will become better understood with reference to the following drawings, description, and claims.

BRIEF DESCRIPTION OF THE DRAWINGS

FIG. 4 illustrates the back view of the flushable insert, including the opening that receives the attachment ring of the faceplate and the surrounding tabs;

FIG. 5 illustrates the front view of the flushable insert, including the slot that fits over the catch on the attachment ring of the faceplate.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the current invention includes devices and systems for a colostomy appliance and methods for using the appliance. In particular, the present invention relates to a colostomy appliance that has been modified to accommodate a flushable insert that can be removed and replaced without removing the outer colostomy bag, allowing for quicker, easier, and more sanitary disposal of fecal waste.

Figure 1:
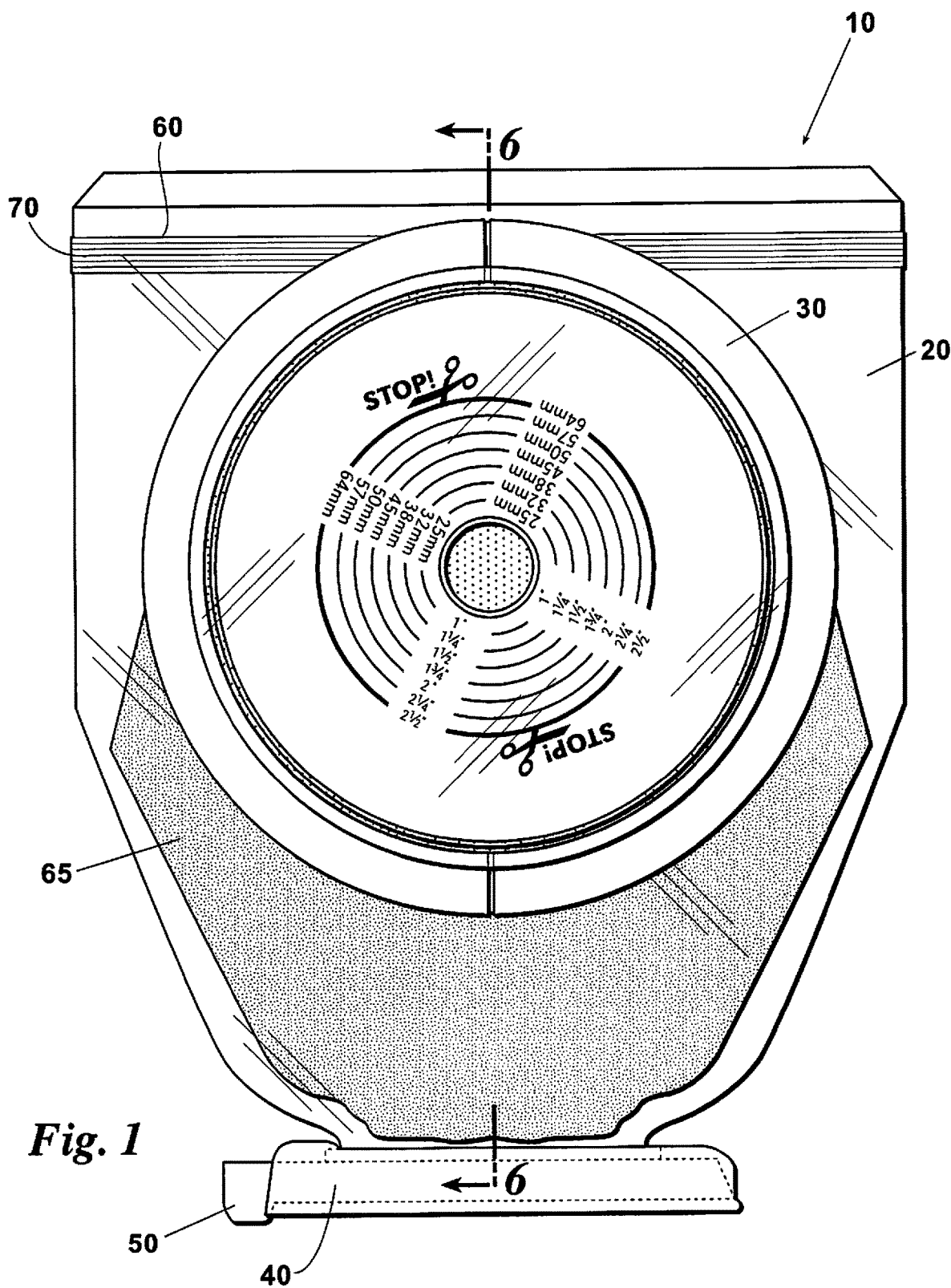
FIG. 1 illustrates the back view, facing toward the patient's body, of the modified colostomy appliance, showing the outer colostomy bag, the faceplate, including the portion of the faceplate that adheres to the patient's skin, and the flushable insert.
Figure 2:
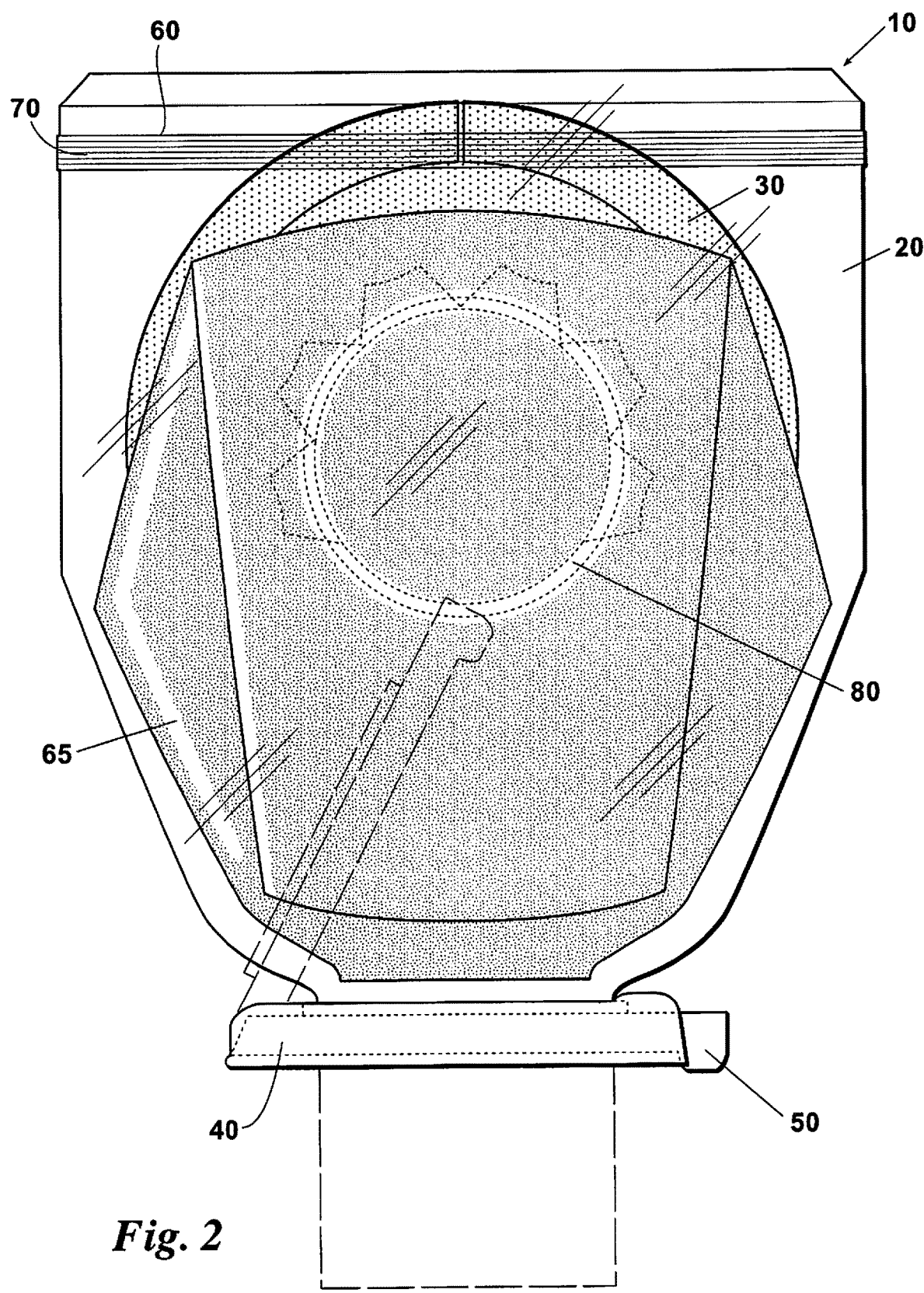
FIG. 2 illustrates the front view, facing away from the patient's body, of the modified colostomy appliance, showing the outer colostomy bag, the faceplate, and the flushable insert.
Figure 3:
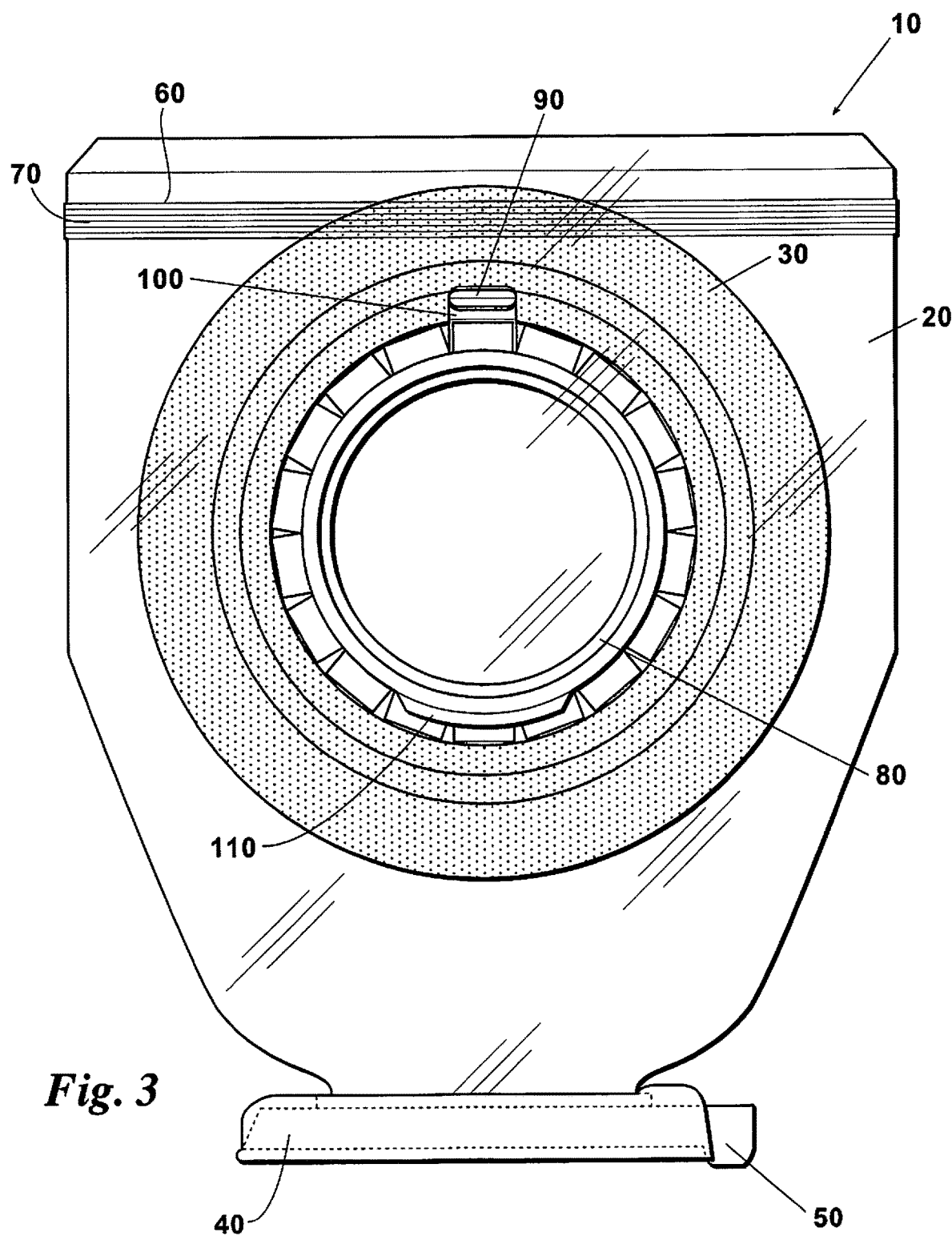
FIG. 3 illustrates the front view of the modified colostomy appliance with the flushable insert removed, showing the attachment ring of the faceplate.

As shown in FIGS. 1-3, the colostomy appliance 10 of the present invention is comprised of an outer colostomy bag 20 and a modified faceplate 30. If the patient uses a two-piece system, the outer colostomy bag 20 may be connected to the faceplate 30 by any method that is known in the art. The outer colostomy bag 20 is comprised of plastic or some other waterproof material that cannot be flushed down the toilet for disposal. The bottom of the outer colostomy bag 20 of the present invention is narrower than the bottom of a standard colostomy bag. As an example, the outer colostomy bag 20 may have a width of approximately 6 inches at the top and taper, either gradually or in one or more steps, to a width of approximately 2 inches at the bottom. The outer colostomy bag has an opening at the bottom 40 that can be temporarily closed to form a water-tight seal. Potential materials that can be used to form the water-tight seal include, but are not limited to, zippers and reusable clips. The outer colostomy bag also has an opening at the top 60 to accommodate the placement and removal of the flushable inserts 65. The top opening 60 of the outer colostomy bag 20 can be sealed by any standard method that allows the bag to be opened and closed quickly and easily. Potential methods include, but are not limited to, plastic zippers, sliding zippers, hook-and-loop fasteners such as Velcro, and folding the top of the bag over onto itself. In the embodiment shown in FIGS. 1-3, the top opening 60 of the outer colostomy bag 20 is sealed with a sliding zipper 70, while the bottom opening 40 of the outer colostomy bag 20 is sealed with a reusable clip 50.

The faceplate 30 of the present invention may be any standard faceplate, where the side of the faceplate that faces away from the patient has been modified to include an attachment ring 80 as shown in FIG. 2 and FIG. 3. The attachment ring may be a separate piece that is connected to the faceplate or the faceplate and ring can be manufactured as a single unit. The height of the attachment ring 80 must be sufficient to secure the flushable insert 65 in place, but should otherwise be minimized so that the overall height of the colostomy appliance 10 is as small as possible. For example, the height of the attachment ring 80 may be approximately ⅜ inch, which creates a corresponding rise from the faceplate 30 of ¼ inch. A catch 90 is connected to the top of the attachment ring 80 by an arm 100, while the bottom of the attachment ring 80 has a lip 110 that extends beyond the attachment ring 80. The catch 90 and the lip 110 are both used to properly align and secure the flushable insert 65 inside the outer colostomy bag 20.

As shown in FIG. 4 and FIG. 5, the flushable insert 65 consists of a front panel 120 and a back panel 130, where the side and bottom edges of each panel have been sealed together to form a pouch. The flushable insert 65 may be made of any material that can contain the fecal material and that can be flushed down the toilet for disposal. Such materials may include, but are not limited to, cellulose papermaking fibers bonded together with a wet strength agent such as used in wet wipes. The inner and/or outer surfaces of each panel may be covered with a waterproof coating to further prevent leakage, as long as such coating does not negatively affect the flushability of the insert.

The flushable insert 65 should be sized so that it fits within the outer colostomy bag 20. As shown in FIG. 4, a circle of material has been removed from the back panel 130 of the flushable insert 65 to form an opening 140 that receives the attachment ring 80. A portion of the bottom rim 150 of the opening 140 is tucked under the lip 110 of the attachment ring 80 in order to align the flushable insert 65 and to secure it in position inside the outer colostomy bag 20. Some or all of the remaining portion of the opening's rim 150 may support tabs 160 that serve to separate the faceplate 30 from the fecal material as it enters the flushable insert 65 and to prevent contamination of the patient's hands during insert changes. The back panel 130 of the flushable insert 65 may also include an upper portion 180 above the opening 140 that can be folded over the front panel 120 to create a sanitary grip when the flushable insert 65 is removed from the outer colostomy bag 20. As shown on FIG. 5, the front panel 120 of the flushable insert 65 has a slot 170 near its top. This slot 170 may be reinforced, either by adding additional layers of material 190 or by any other known method, and is designed to fit over the catch 90 on the attachment ring 80, further aligning the flushable insert 65 and securing it in place.

Figure 6:
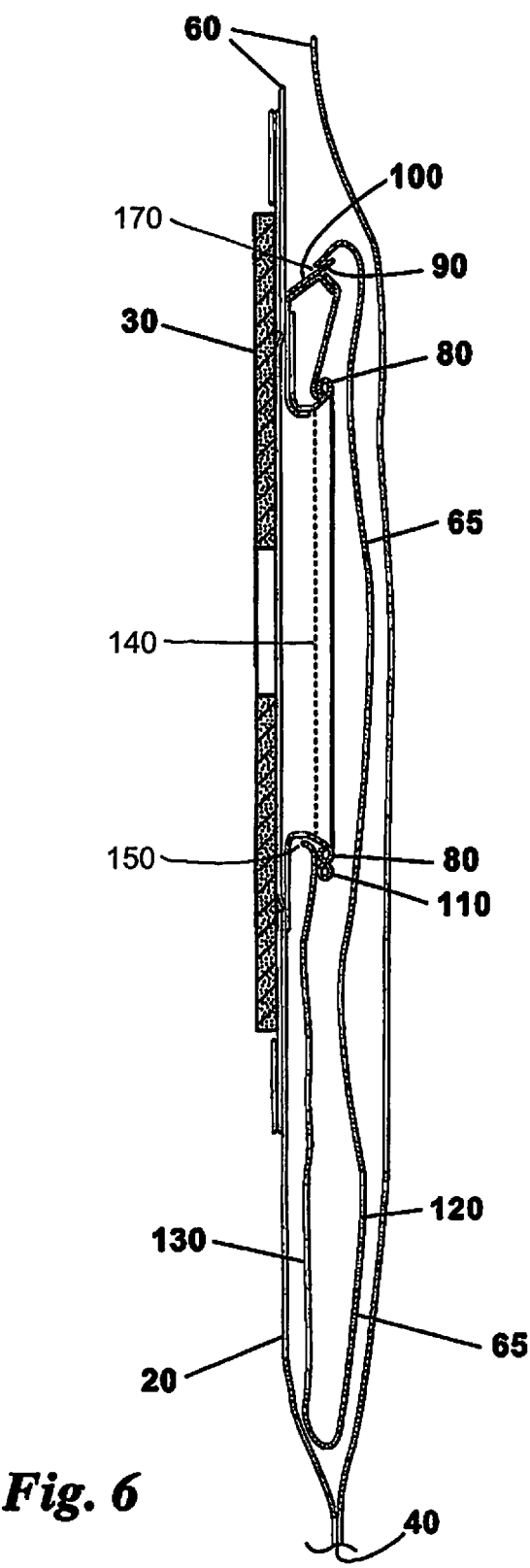
FIG. 6 is a cross-sectional view taken along the line 6-6 of FIG. 1.

FIG. 6 is a cross-sectional view through the center of the modified colostomy appliance 10. As shown in FIG. 6, the slot 170 in the front panel 120 of the flushable insert 65 fits over the catch 90 of the attachment ring 80, with the portion of the front panel 120 above the slot 170 tucked into the space between the catch 90 and the attachment ring 80. The bottom rim 150 of the opening 140 in the back panel 130 of the flushable insert 65 is tucked under the lip 110 of the attachment ring 80.

In order to use the present invention, a patient attaches the modified faceplate 30 to his or her body through standard means. If the patient uses a two-piece system, an outer colostomy bag 20 is then attached to the faceplate 30 using any standard method. Alternatively, if the patient uses a one-piece system, the outer colostomy bag 20 will already be attached to the faceplate 30. The patient opens the top of the outer colostomy bag 20, places a flushable insert 65 inside the outer colostomy bag 20, and aligns the opening 140 in the back panel 130 of the flushable insert 65 with the attachment ring 80 of the faceplate 30. The flushable insert 65 is secured in place by tucking a portion of the bottom rim 150 of the opening 140 under the lip 110 of the attachment ring 80 and by hooking the slot 170 in the front panel 120 of the flushable insert 65 over the catch 90 at the top of the attachment ring 80. The patient temporarily closes the top of the outer colostomy bag 20, and fecal waste passes through the stoma into the interior of the flushable insert 65 without contacting the attachment ring 80, faceplate 30, or outer colostomy bag 20. The appliance 10 is then worn until the flushable insert 65 is ready for removal.

In order to remove the used flushable insert 65 and replace it with a new one, the patient opens the top of the outer colostomy bag 20 and disconnects the flushable insert 65 from the catch 90 on the attachment ring 80. The patient then folds the upper portion 180 of the back panel 130 of the flushable insert 65 over the insert's front panel 120 to seal the top of the flushable insert 65 and to create a sanitary grip, removes the flushable insert 65 from the outer colostomy bag 20, and disposes of the flushable insert 65 by flushing it down the toilet. Because the flushable insert 65 is held in place only by the catch 90 and the lip 110 of the attachment ring 80, it can be removed quickly and easily without the need for any additional materials or supplies. The patient then places and aligns a new flushable insert 65 in the outer colostomy bag 20 as described above. The outer colostomy bag 20 remains in place throughout the entire process.

When necessary, the outer colostomy bag 20, which has not been contaminated by fecal waste, can be thrown away as garbage. Even if the outer colostomy bag 20 becomes soiled by liquid feces that penetrate the flushable insert 65, most of the fecal material will still be contained inside the flushable insert 65, which may be removed and flushed as described above. The outer colostomy bag 20 may then be effectively rinsed clean with a minimal amount of water using the bottom opening 40 of the outer colostomy bag 20. As a result, it is not necessary to change the outer colostomy bag 20 in this situation.

The modified colostomy appliance and flushable insert can be used with one- and two-piece systems. In addition, the invention can be used with standard faceplates, methods of securing the faceplate to a patient's body, and methods of sealing the bottom of the colostomy bag. As a result, it is compatible with and suitable for a wide range of applications in the ostomy field.

From the foregoing, it will be understood by persons skilled in the art that a modified colostomy appliance and a flushable insert that can be removed and replaced without removing the outer bag have been provided. A method for using the above-described system has also been provided. The invention is relatively simple and easy to manufacture, yet affords a variety of uses. While the description contains many specifics, these should not be construed as limitations on the scope of the invention, but rather as an exemplification of the preferred embodiments thereof. The foregoing is considered as illustrative only of the principles of the invention. Further, because numerous modifications and changes will readily occur to those skilled in the art, it is not desired to limit the invention to the exact construction and operation shown and described, and accordingly all suitable modifications and equivalents may be resorted to, falling within the scope of the invention. Although this invention has been described in its preferred form with a certain degree of particularity, it is understood that the present invention of the preferred form has been made only by way of example and numerous changes in the details of construction and combination and arrangement of parts may be resorted to without departing from the spirit and scope of the invention.

We claim:

1. A colostomy appliance comprising
a faceplate with an attachment ring, the attachment ring having a lip only in a lower portion of the attachment ring and a catch only in an opposite upper portion of the attachment ring, the catch connected to the attachment ring by an arm, the lip and catch separated from each other by a diameter of the attachment ring;
an outer colostomy bag connected to the faceplate, the outer colostomy bag comprised of a waterproof material and having a top opening that can be temporarily closed and a bottom opening that can be temporarily closed; and
an insert comprised of a flushable material, the insert having an opening that fits over the attachment ring;
wherein the lip and the catch of the attachment ring are used to align and secure the insert in position inside the outer colostomy bag.

2. A colostomy appliance according to claim 1, wherein a means for sealing the top opening is selected from the group consisting of plastic zippers, sliding zippers, hook-and-loop fasteners, and folding a top of the outer colostomy bag over onto itself.

3. A colostomy appliance according to claim 1, wherein a means for sealing the bottom opening is selected from the group consisting of plastic zippers, sliding zippers, and reusable clips.

4. A colostomy appliance according to claim 1, wherein a top of the outer colostomy bag has a width of approximately 6 inches and a bottom of the outer colostomy bag has a width of approximately 2 inches, the width tapering from top to bottom gradually or in one or more steps.

5. A colostomy appliance according to claim 1, wherein the outer colostomy bag is comprised of plastic or some other waterproof material.

6. A colostomy appliance according to claim 1, wherein the attachment ring has a height of approximately ⅜ inches.

* * * * *